United States Patent
Hoejvang-Nielsen

(10) Patent No.: US 9,763,464 B2
(45) Date of Patent: Sep. 19, 2017

(54) POTASSIUM CONTAINING PREPARATION, PROCESS FOR THE PRODUCTION THEREOF AND USE THEREOF

(71) Applicant: Leif Hoejvang-Nielsen, Fredensborg (DK)

(72) Inventor: Leif Hoejvang-Nielsen, Fredensborg (DK)

(73) Assignee: Boehringer Ingelheim Vetmedica GmbH, Ingelheim am Rhein (DE)

( * ) Notice: Subject to any disclaimer, the term of this patent is extended or adjusted under 35 U.S.C. 154(b) by 850 days.

(21) Appl. No.: 13/971,941

(22) Filed: Aug. 21, 2013

(65) Prior Publication Data
US 2014/0057022 A1    Feb. 27, 2014

(30) Foreign Application Priority Data
Aug. 24, 2012 (EP) .................................. 12181800

(51) Int. Cl.
| A23K 1/175 | (2006.01) |
|---|---|
| A61K 9/00 | (2006.01) |
| A23K 20/105 | (2016.01) |
| A23K 20/22 | (2016.01) |
| A23K 20/24 | (2016.01) |
| A23K 20/20 | (2016.01) |
| A23K 50/10 | (2016.01) |

(52) U.S. Cl.
CPC .......... *A23K 1/1751* (2013.01); *A23K 20/105* (2016.05); *A23K 20/22* (2016.05); *A23K 20/24* (2016.05); *A23K 20/30* (2016.05); *A23K 50/10* (2016.05); *A61K 9/0068* (2013.01)

(58) Field of Classification Search
CPC ........ A23K 20/20; A23K 40/30; A23K 40/35; A23K 50/10; A23K 10/40; A23K 40/10; A23K 20/22; A23K 20/24; A61K 9/0068
USPC ................ 424/438; 426/2, 74, 515; 514/769
See application file for complete search history.

(56) References Cited

U.S. PATENT DOCUMENTS

| 4,976,963 A | 12/1990 | Schricker et al. |
|---|---|---|
| 5,958,464 A | 9/1999 | Register |
| 2010/0303913 A1* | 12/2010 | Gheith .................. A61K 9/5169 424/488 |
| 2011/0294860 A1* | 12/2011 | Tatsumi ................... A61K 9/06 514/356 |
| 2012/0142531 A1* | 6/2012 | Mazeaud .............. A23L 1/0029 504/117 |

FOREIGN PATENT DOCUMENTS

| CN | 102550832 A | 7/2012 |
|---|---|---|
| FR | 2851423 A1 | 8/2004 |

OTHER PUBLICATIONS

Vrana, L. M. and Staff, U. b. 2014. Calcium Chloride. Kirk-Othmer Encyclopedia of Chemical Technology. 1-13.*
Abstract in English of CN102550832, 2012.
Abstract in English of FR2851423, 2004.
Mueller et al., "Effect of Potassium Supplementation by Fertilization and KCl Bolus on Mineral Metabolism in Lactating Beef Cows". Journal of the American College of Nutrition, vol. 8, No. 5, Abstract 33, 1989, p. 432.
Peek et al., "Hypokalemia, Muscle Weakness, and Recumbency in Diary Cattle". Veterinary Therapeutics: Research in Applied Veterinary Medicine, vol. 1, No. 4, Fall 2000, pp. 235-244.
Sweeney, Raymond W., "Treatment of Potassium balance disorders". Fluid and Electrolyte Therapy, vol. 15, No. 3, Nov. 1999, pp. 609-617.

* cited by examiner

*Primary Examiner* — Walter Moore
(74) *Attorney, Agent, or Firm* — Paula K. Wittmayer; Wendy M. Gombert

(57) ABSTRACT

The invention is directed to a potassium containing preparation or potassium bolus for the prevention or treatment of potassium deficit and optionally other deficit of minerals in ruminants, a process for the production thereof as well as the use thereof. The present invention makes it possible to provide a potassium containing preparation or potassium bolus with a high content of up to 70 wt.-% of potassium salt, based on the total weight of the potassium containing preparation, by adding only a relatively small amount of calcium chloride (15 to 40 wt.-%) and water (10 to 22 wt.-%) to the potassium salt.

32 Claims, No Drawings

POTASSIUM CONTAINING PREPARATION, PROCESS FOR THE PRODUCTION THEREOF AND USE THEREOF

FIELD OF THE INVENTION

The present invention relates to a potassium containing preparation or potassium bolus, a process for the production thereof and the use thereof.

BACKGROUND OF THE INVENTION

It is well known that dairy cows during specific periods of their life and/or under specific management or disease conditions face short periods, where they have an increased requirement for specific minerals such as calcium (Ca) and/or phosphorous (P) and/or potassium (K). For example, like sodium (Na), cattle need potassium (K) in large amounts to maintain normal body and organ function. Potassium works in conjunction with Na in the body to transport nutrients in and out of cells.

Potassium is the third most abundant mineral in the body and of major importance to the functioning of nerve cells and muscle cells. Hypokalemia may cause reduced gastro intestinal motility, reduced feed intake, reduced water intake, reduced body weight, dehydration, reduced milk yield and muscular weakness which may ultimately lead to recumbency.

As only little potassium storage occurs in the bovine body, potassium must be supplied daily in the diet. In cows off feed or with in-appetence therefore the reduced feed intake leads to reduced potassium supplementation, which may soon lead to hypokalemia.

Hypokalemia is particularly relevant for instance to fresh cows off feed and sick cows such as cows with displaced abomasum or other diseases causing the cow to become very sick and in-appetent or anorexic.

In order to avoid the above deficiencies the increased requirements for specific minerals are normally met with oral supplements of the single mineral in question. Such supplements are well known in the market, where they exist in the form of boluses or gels (calcium), boluses or drenches (phosphorous) or powders (potassium).

A preferred salt for the potassium supplement is potassium chloride, because of the high content of potassium in this salt, the very good solubility in water and the alkalizing effect of the chloride.

Since potassium chloride has a very unpleasant bitter tasting, usually the animals must be force-treated. In the case aqueous solutions are to be given, this may cause the potassium chloride to enter the lungs, which may be fatal to the animal. Furthermore, the use of a potassium containing gel results in dosage problems due to difficulties associated with the discharge of the gel from the container. In addition, also a gel provides the unpleasant taste. Using capsules containing potassium in powder form is also possible. However, the potassium content of such capsules is very low so that a considerable number of capsules must be given to the animal to be treated within relatively short intervals of time which is not practicable.

A preferred administration form is the solid bolus, since it is easy to administer, there is no waste and the risk of aspiration, whereby the product is drawn down the trachea, is significantly reduced. For a potassium supplement such as a potassium bolus the preferred amount of potassium is around 50 g per dose.

However, it is not possible today with any known technique to make solid boluses with a content of potassium chloride equal to or higher than approximately 40% (w/w). With such a low inclusion rate it is not possible to include the required content of potassium because the bolus becomes too big for the ruminant, e.g. a cow, to swallow. Consequently, there are no solid potassium boluses available in the market place today. Instead the products used are large gelatin capsules with pure potassium chloride, e.g. "C for Kalium" from the French company LPG.

In the prior art solid preparations having a high calcium content and which can be administered easily with precise dose adjustments are already known. For example, in the U.S. Pat. No. 5,395,622 it is described a method of providing dosage units containing calcium for administering to ruminants to treat hypocalcemia, said method comprising the steps of (a) mixing $CaCl_2.xH_2O$ and $CaSO_4.yH_2O$, x being a number greater than 0 and lower than 6 and y being a number equal to or greater than 0 and lower than or equal to 2, the weight ratio of $CaCl_2.xH_2O$ to $CaSO_4.yH_2O$ being from 1:0.05 to 1:2.4, to form a homogeneous mixture, (b) adding water to said homogeneous mixture to provide a mass which will flow through a funnel having a neck diameter of 10 mm at 40° C., the amount of water not exceeding the amount needed to convert $CaCl_2.xH_2O$ to $CaCl_2.6H_2O$ and $CaSO_4.yH_2O$ to $CaSO_4.2H_2O_9$, (c) introducing said mass into a plurality of casting moulds, and (d) subjecting said mass contained in said moulds to a temperature such that said mass solidifies therein into a solid mass containing a mixture of $CaCl_2$ and $CaSO_4$ hydrates.

Therefore, this calcium chloride containing preparation or calcium bolus is produced by solidification of a mixture of calcium chloride and calcium sulfate, which both exist in different hydration forms, i.e. both having different amounts of crystal water. By using such salts with low amounts of crystal water, adding a small amount of water and heating above the indicated temperature, where the crystal water is liberated, it is possible to get a liquid mass, which transforms into a solid mass, when it is cooled again. This product is also known under the trade name BOVIKALC®.

The same technique as disclosed in U.S. Pat. No. 5,395,622 cannot be used for making a potassium containing preparation or potassium bolus, since there are potassium salts such as potassium chloride that does not contain crystal water and therefore it is difficult to convert theses salts into the solid state again.

Further prior art is as follows:

Mueller F J et al. (Journal of the American College of Nutrition 1989, 8(5): 432) describe the effect of potassium supplementation by fertilization and potassium chloride bolus on mineral metabolism in lactating beef cows.

Sweeney R W (The Veterinary Clinics of North America. Food animal Practice November 1999, 15(3): 609-617) relates to the treatment of potassium disorders.

Peek S F et al. (Veterinary Therapeutics: Research in Applied Veterinary Medicine Fall 2000, 1(4): 235-244) is directed to hypokalemia, muscle weakness, and recumbency in diary cattle.

U.S. Pat. No. 4,976,963 deals with ruminant feed antacid containing potassium, sodium and chlorine.

FR Patent No. 2 851 423 discloses controlled diffusion ruminant feed bolus production, by mixing liquid and solid components and compression molding, useful for prolonged release of minerals, trace elements and vitamins.

CN Patent No. 102 550 832 relates to an animal feed additive and a preparation method thereof.

U.S. Pat. No. 5,958,464 describes a composition for preventing and treating milk fever in freshening cows, and a method of administering the composition.

It is therefore an object of the present invention to avoid the disadvantages of prior art and to provide a solid and easily doseable preparation having a high potassium content (>40% (w/w)) which may be readily administered to ruminants.

DESCRIPTION OF THE INVENTION

Surprisingly, it has been found that a combination of calcium chloride, water and a potassium salt makes it possible to obtain a solid mass or bolus with an unexpected high content of potassium salt which may be readily administered to ruminants such as cattle, sheep and goats, preferably cattle or bovine, particularly preferred cows, especially dairy cows.

According to the present invention it is therefore provided a process for the production of the potassium containing preparation or potassium bolus suitable for the prevention or treatment of potassium deficit and optionally other deficit of minerals in ruminants, comprising the following steps (a) mixing $CaCl_2.xH_2O$, wherein x=0, 1, 2 or 4 or mixtures thereof, and water and heating the mixture to a temperature in the range of from 65 to 100° C., preferably 75 to 85° C., and even more preferred 80° C. until the crystal water is released and the salt is completely dissolved;

(b) adding a potassium salt and optionally one or more mineral salts which is/are no potassium salt(s) and heating until the temperature is again in the range of from 65 to 100° C., preferably 75 to 85° C., and even more preferred 80° C.;

(c) maintaining the mixture at the temperature adjusted in step (b) under mixing, preferably constant mixing, to keep the potassium salt and optionally the one or more mineral salts in a homogeneous suspension;

(d) forming the suspension into a suitable form and cooling it to a temperature in the range of from 15° C. to 30° C., preferably 17° C. to 28° C., 19° C. to 27° C., even more preferred 20° C. to 25° C. to obtain a solid mass.

The process according to the present invention provides the potassium containing preparation or potassium bolus of the invention. The process of the present invention is possible because the potassium salt, even if it is highly soluble in water, does not go into solution because the affinity of calcium chloride to water is even higher. It is presumed that all the water present is used as crystal water in the crystallization of the calcium chloride and the potassium salt is embedded in the solid calcium chloride crystals. Therefore, the essential aspect of the present invention is considered to be the solidification of the potassium containing preparation which is the result of the bonding of the water present in the form of crystal water.

Also the potassium containing preparation or potassium bolus is subject of the present invention. It is therefore provided a potassium containing preparation or potassium bolus suitable for the prevention or treatment of potassium deficit and optionally other deficit of minerals in ruminants, preferable cows, comprising the following composition:

potassium salt: 40 to 70 wt.-%,
  preferably >40 to 70 wt.-%,
  more preferably 45 to 70 wt.-%;
$CaCl_2.xH_2O$, wherein x=0, 1, 2 or 4 or mixtures thereof:
  15 to 40 wt.-%,
  preferably 25 to 35 wt.-%;
water: 10 to 22 wt.-%,
  preferably 11 to 18 wt.-%;
mineral salt(s): 0 to 15 wt.-%,
  preferably 0 to 12 wt.-%;
the values of wt.-% are based on the total weight of the potassium containing preparation or potassium bolus, wherein the potassium salt is embedded in the solid calcium chloride crystals.

According to a preferred embodiment of the present invention it is provided a potassium containing preparation or potassium bolus suitable for the prevention or treatment of potassium deficit and optionally other deficit of minerals in ruminants, preferably cows, comprising the following composition:

potassium salt, preferably potassium chloride: 50 to 55 wt.-%;
$CaCl_2.2H_2O$: 22 to 28 wt.-%;
water: 12 to 18 wt.-%;
mineral salt(s), preferably magnesium oxide: 5 to 12 wt.-%;
the values of wt.-% are based on the total weight of the potassium containing preparation or potassium bolus, wherein the potassium salt is embedded in the solid calcium chloride crystals.

According to another preferred embodiment of the present invention it is provided a potassium containing preparation or potassium bolus suitable for the prevention or treatment of potassium deficit and optionally other deficit of minerals in ruminants, preferably cows, comprising the following composition:

potassium salt, preferably potassium chloride: 40 to 60 wt.-%;
$CaCl_2.2H_2O$: 25 to 40 wt.-%;
water: 10 to 16 wt.-%;
mineral salt(s), preferably magnesium oxide: 0 to 12 wt.-%;
the values of wt.-% are based on the total weight of the potassium containing preparation or potassium bolus, wherein the potassium salt is embedded in the solid calcium chloride crystals.

The term "embedded" in the context of the present invention is to be understood in that the potassium salt and any other mineral salts is incorporated into the crystal structure formed by the $CaCl_2$ crystals.

Due to the selected administration form for the potassium supplement as bolus, a simple administration and precise dose adjustment is achieved, no waste is produced and the risk of aspiration of the potassium bolus into the lungs of the animal is avoided in practice. Since the potassium salt such as potassium chloride is embedded in the solid calcium chloride crystal the unpleasant, bitter tasting of the potassium salt is masked, so that there will arise no problems during the administration to the animals at all.

According to the present invention a "bolus" represents a drug, medication or other product in the form of a single, large dose which is in solid form and is to be administered orally. The bolus according to the present invention and in accordance with veterinary medicine is preferably a large time-release tablet that stays in the rumen of cattle or bovine. The bolus is given to raise the concentration of the contained potassium and optionally other minerals in blood to an effective level. It is a matter of course that the bolus dose depends on the systemic levels of the contents desired throughout the animal body. Other forms of the bolus for the administration by intravenously, by intramuscular, intrathecal or subcutaneous injection is not intended according to the present invention, the oral administration is the favored route of administration.

In the following, the process of an embodiment of the present invention to produce the potassium containing preparation or potassium bolus will be described in detail. It is a matter of course that the explanations of the process apply mutatis mutandis to the potassium containing preparation per se.

In process step (a) the calcium chloride and water are mixed and the mixture is heated to a temperature in the range of from 65 to 100° C., preferably 75 to 85° C., and even more preferred 80° C. until the crystal water is released and the salt is completely dissolved. The calcium chloride used is $CaCl_2.xH_2O$, wherein x=0, 1, 2 or 4 or mixtures thereof. Calcium chloride exists as anhydride (0 $H_2O$) or with 1, 2, 4 or 6 molecules of crystal water. In the process of the present invention $CaCl_2$ is used in a low hydration or anhydride form and sufficient water is added to convert all or part of the $CaCl_2$ to a higher hydration form. Therefore the calcium chloride in form of the anhydride, monohydrate, dihydrate or tetrahydrate or mixtures thereof may be used as starting material. Particularly preferred is to employ $CaCl_2.2H_2O$.

In step (a) the weight ratio of calcium chloride and water is preferably adjusted to be from 4:5 to 3:1, preferably 3:2 to 5:2, and even more preferred 5:3.

The temperature used is adjusted to be in the range of from 65 to 100° C., preferably 75 to 85° C., and even more preferred 80° C. It is practicable if the boiling temperature of water is not reached, i.e. the temperature is preferably below 100° C. in order to prevent the evaporation of water which is added. Therefore, the temperature used is preferably adjusted to be in the range of from 65 to 99° C., more preferred 75 to 85° C., and even more preferred 80° C. Thus, the water added in or during step (a) of the inventive process is preferably not lost during the process, i.e. all extra water is preferably absorbed as extra crystal water by the $CaCl_2$.

According to process step (b) the potassium salt is added and it is heated until the temperature is again in the range of from 65 to 100° C., especially 65 to 99° C., preferably 75 to 85° C., and even more preferred 80° C.

The potassium salt is preferably added in an amount of 40 wt.-% to 70 wt.-%, especially >40 wt.-% to 70 wt.-%, preferably 50 wt.-% to 70 wt.-%, >40 wt.-% to 60 wt.-%, 55 wt.-% to 70 wt.-%, 51 wt.-% to 59 wt.-%, 53 wt.-% to 57 wt.-% or 55 wt.-% to 60 wt.-%, even more preferred 45 wt.-% to 60 wt.-%, 51 wt.-% to 59 wt.-%, 53 wt.-% to 57 wt.-% or 55 wt.-% to 60 wt.-%, based on the total weight of the potassium containing preparation. Therefore the potassium salt is preferably added in an amount of at most 70 wt.-%, based on the total weight of the potassium containing preparation.

Any potassium salt which may be used in animal feed or in animal health may be used according to the present invention. A potassium salt having a high potassium content is preferred. Furthermore, the potassium salt used shall be water-soluble. A salt is defined to be water-soluble in the temperature range of 15 to 25° C. if the following requirements are fulfilled:
Very easily soluble: <1 ml solvent needed per g substance to result in a solution;
Easily soluble: 1 to 10 ml solvent needed per g substance to result in a solution; and
Soluble: 20 to 30 ml solvent needed per g substance to result in a solution.

That is the potassium salt is considered to be water-soluble in case a maximum of 30 ml water per g potassium salt is necessary to provide a solution of the potassium salt in water in the temperature range of 15 to 25° C.

Illustrative examples are potassium chloride, potassium bromide, potassium iodide, potassium sulfate, potassium nitrate, potassium phosphate, di-potassium phosphate, tri-potassium phosphate, and potassium citrate, preferably potassium chloride, potassium sulfate, di-potassium phosphate, tri-potassium phosphate, and potassium citrate. Particularly preferred is a potassium salt having no crystal water when crystallized such as potassium chloride, potassium sulfate, di-potassium phosphate, tri-potassium phosphate but also a potassium salt having crystal water such as potassium citrate monohydrate may be used. Since the potassium citrate monohydrate does not exist in a higher hydration form, it can not be used per se in the process according to the U.S. Pat. No. 5,395,622 as discussed above. Particularly preferred in the present invention is potassium chloride.

The temperature used in step (a) or step (b) may be the same or may be different. It is, however, preferred to use the same temperature in step (a) and step (b).

According to a preferred embodiment the potassium salt and one or more mineral salts is/are added in step (b) and it is heated until the temperature is again in the range of from 65 to 100° C., preferably 75 to 85° C., and even more preferred 80° C.

Under certain conditions it may be desired to include other salts besides the potassium salt in the potassium containing preparation or potassium bolus, i.e. one or more mineral salts which are—as a matter of course—no potassium salts.

The expression "mineral salts" or "minerals" should be understood in the context of the present invention, just as used in the field of nutrition science, to be synonymous to mineral nutrients which stand for different nutrient matter. The expression should include inorganic salts as well as organic salts such as sodium citrate. The two kinds of minerals are macrominerals and trace minerals. The class of macrominerals is required in larger amounts than trace minerals, and usually is expressed as a percentage of the diet or grams per day, rather than parts per million (ppm). The minerals and trace elements used may be for example selected from salts of copper (Cu), magnesium (Mg), iron (Fe), zinc (Zn), iodine (I), selenium (Se), manganese (Mn), fluoride ($F^-$), chromium (Cr), molybdenum (Mo), sodium (Na), phosphorus (P), sulfur (S), chloride ($Cl^-$), and mixtures thereof. Additional minerals which are less preferred are arsenic (As), nickel (Ni), silicon (Si), boron (B), cadmium (Cd), lead (Pb), lithium (Li), tin (Sn), vanadium (V) and cobalt (Co as part of vitamin B12) salts, and mixtures thereof. The source of the mineral salts used may be any of the well known salts such as carbonate, oxide, hydroxide, chloride, sulfate, phosphate, gluconate, lactate, acetate, fumarate, citrat, maleate, malate, amino acids and the like for the cationic minerals and sodium, potassium, calcium, magnesium and the like for the anionic minerals. The minerals may be present in nutritional relevant amounts depending on the intended use thereof. Those skilled in the art are familiar with the preferred ranges for animals. It is clear that the daily intake of minerals may vary with the intended use so that no exact dosages may be mentioned. Besides the above-listed minerals also other mineral salts may be used, e.g. commercially available mixtures. For example, also a calcium product containing one or more mineral salts may be used, e.g. CALCITRACE® from the UK company Norbrook which contains small amounts of magnesium and phosphorous salts.

According to a particularly preferred embodiment the mineral salt used is a magnesium salt. A preferred magnesium salt is magnesium chloride, magnesium oxide or magnesium hydroxide, particularly preferred is magnesium oxide.

In process step (c) the mixture is maintained at a temperature in the range of from 65 to 100° C., preferably 75 to 85° C., and even more preferred 80° C. under mixing, preferably constant mixing, to keep the potassium salt and optional mineral salt(s) in a homogeneous suspension. A constant mixing procedure is particularly preferred in order to obtain a more homogeneous suspension. The suspension is considered to be homogeneous if the achieved appearance thereof is uniform in composition, i.e. no heterogeneity may be observed by visual examination.

Any mixing device may be used in the process according to the present invention which allows heating. The skilled person is familiar with the technical equipment that may be used.

The temperature of step (c) is the same or may be different as in step (b) and/or step (a). It is, however, preferred to use the same temperature in step (a), step (b) and step (c).

Subsequently, in step (d) the obtained suspension is formed into a suitable form, e.g. a usually known bolus shape, for example filled into a suitable form, and it is allowed to cool to a temperature in the range of from 15° C. to 30° C., preferably 17° C. to 28° C., 19° C. to 27° C., even more preferred 20° C. to 25° C. In order to speed up the cooling procedure it might be purposive to adjust a very low temperature such as 2 to 5° C. to reach the end temperature of the solid mass very quickly.

After cooling the mixture becomes a solid mass. The solid mass may be removed from the form or it may be filled or cast in a form that can be given on the whole (solid mass+form) to the cattle or bovine. For example, the used material of the form may be selected from a material which is subsequently removed from the solid mass or bolus such as cardboard, so that the solid mass or bolus is per se administered to a ruminant, preferably a cow. Also a material may be used which is not removed from the solid mass or bolus and is administered together with the solid mass or bolus to the ruminant, preferably a cow, such as gelatine.

Optionally, the potassium containing preparation of one exemplary embodiment of the present invention can be obtained as a final formulation in the form of a bolus which may be subjected to an additional coating step [optional and additional step (e)]. For example the bolus may be dipped and covered in some kind of a coating material, for example some type of wax or another commonly used coating, before it is administered to the ruminant.

The expression "dietary supplement" or "supplement" as used hereinabove and herein below includes a composition which may be used without prescription by a third party, for example a veterinary. The composition may be taken together with meals or separated thereof, on a daily basis or only sometimes. Dietary supplements are primarily important for individuals having inadequate diets, with a reduced ability to utilize or absorb the essential substances from food, or for the prevention, management and treatment of health conditions of animals in need thereof.

In another embodiment the present invention is also directed to the use of a potassium containing a preparation in the form of a solid bolus as an oral dosage form or dietary supplement for the prevention or treatment of potassium deficit and optionally other deficit of minerals in ruminants, preferably cows. Furthermore, corresponding methods of treatment, uses for the preparation of a pharmaceutical composition for the prevention or treatment of potassium deficit and optionally other deficit of minerals in ruminants, preferably cows, and potassium containing preparations according to the present invention in form of a solid bolus as an oral dosage form or dietary supplement for use in a method of prevention or treatment of potassium deficit and optionally other deficit of minerals in ruminants, preferably cows, are also intended to be within the spirit of the present invention.

The advantages of the present invention are manifold:

According to one embodiment the present invention is provided as a potassium supplement with a content of potassium salt in the quantity of or higher than approximately 40 wt.-%, i.e. in the range of 40 to 70 wt.-%, preferably >40 to 70 wt. %, based on the total weight of the potassium containing preparation. Although the potassium salts preferably used such as potassium chloride have no crystal water, the present invention provides an unexpected technique using the crystal water of calcium chloride for making a potassium containing preparation or potassium bolus. That is, the present invention makes it possible to provide a potassium containing preparation or potassium bolus with a high content of up to 70 wt.-% of potassium salt, based on the total weight of the potassium containing preparation, by adding only a relatively small amount of calcium chloride, for example 20 to 40 wt.-%, and water, for example 10 to 20 wt.-%, to the potassium salt. As a rough guide 20 wt.-% $CaCl_2$+10 wt.-% water corresponds to the upper level of the potassium salt (70 wt.-%) and 40 wt.-% $CaCl_2$+20 wt.-% water corresponds to the lower level of the potassium salt (40 wt.-%). The solidification of the preparation is the result of the bonding of the water in the form of crystal water.

Nevertheless, the potassium containing preparation has a high content of potassium, the form and size of the preparation is not too big for the ruminant, preferably cows, to be swallowed.

Moreover, by increasing the ratio between calcium chloride and water, preferably to >5:3, more preferably >5:2, it was surprisingly found that the melting point of the potassium containing preparation according to the present invention can be advantageously increased. Thereby, it is for instance possible to prepare a potassium bolus that is also still solid at elevated temperatures.

Furthermore, the potassium containing preparation of an embodiment of the present invention is a solid preparation having a high potassium content of 40 to 70 wt.-% or >40 to 70 wt.-%, preferably 50 to 70 wt.-%, >40 wt.-% to 60 wt.-%, 55 to 70 wt.-%, 50 to 60 wt.-%, 51 to 59 wt.-%, 53 to 57 wt.-% or 55 to 60 wt.-%, even more preferred 50 to 60 wt.-%, 51 to 59 wt.-%, 53 to 57 wt.-% or 55 to 60 wt.-%, which allows a precise dose adjustment and which is not available on the market up to now.

In addition, the process of producing the potassium containing preparation is a simple process comprising several steps which may be readily carried out by a person skilled in the art.

If desired it is possible to include other mineral salts besides the potassium salt in the potassium containing preparation or potassium bolus. Particularly preferred are magnesium salts such as magnesium chloride, magnesium oxide or magnesium hydroxide. Other mineral salts may also be used.

The obtained solid mass may be directly orally administered to the ruminant such as a cow or it may be subjected to any known coating procedure.

Therefore, the administration form is not limited, any suitable solid dosage form may be used. In embodiments in which the bolus is filled into gelatine capsules, it is a further advantage that the gelatine is not attached by the solid mass used and that a substantially larger amount of potassium may be included as compared to known dosage forms.

Due to the selected administration form for the potassium supplement as a solid bolus, easy administration is achieved, there is no waste, and the risk of aspiration is avoided. Since the potassium salt, such as potassium chloride, is embedded in the calcium chloride, the unpleasant, bitter tasting is masked, and the animals will not refuse the intake of the potassium containing preparation.

It will be readily apparent to those skilled in the art that various changes and modifications of an obvious nature may be made without departing from the spirit of the invention, and all such changes and modifications of an obvious nature may be made without departing from the spirit of the invention, and all such changes and modifications are considered to fall within the scope of the invention, as defined by the claims.

EXAMPLES

In the following examples the process of production of a potassium containing preparation according to the present invention is described.

Example 1

A potassium containing preparation of the present invention having the following composition is produced:
potassium chloride: 51 wt.-%
$CaCl_2 \cdot 2H_2O$: 25 wt.-%
water: 15 wt.-%
magnesium oxide: 9 wt.-%

The general procedure is as follows:
Mix calcium chloride and water and heat to 80° C. until the crystal water is released and the salt is completely dissolved.

Add potassium chloride and the magnesium oxide and heat until the temperature is again 80° C. Maintain the mixture at this temperature under constant mixing to keep the potassium chloride and magnesium salt in a homogeneous suspension.

Fill the mixture into a suitable form—e.g. bolus shape—and allow cooling to room temperature (about 15 to 30° C.).

After cooling the mixture becomes a solid mass. After removing from the form the solid mass is dipped and covered in a coating material before it may be administered to a cow.

Example 2

A potassium containing preparation of the present invention, wherein $CaCl_2$ in anhydrous form is used instead of $CaCl_2 \cdot 2H_2O$ having the following composition is produced:
potassium chloride: 51 wt.-%
$CaCl_2$ (anhydrous): 19 wt.-%
water: 21 wt.-%
magnesium oxide: 9 wt.-%

The general procedure is as follows:
Mix calcium chloride and water and heat to 72 to 80° C. until the salt is completely dissolved.

Add potassium chloride and the magnesium oxide and heat until the temperature is again 72 to 80° C. Maintain the mixture at this temperature under constant mixing to keep the potassium chloride and magnesium salt in a homogeneous suspension.

Form the mixture into a suitable form—e.g. bolus shape—and allow cooling to room temperature (about 15 to 30° C.).

After cooling the mixture becomes a solid mass. The solid mass may be directly administered to a cow as potassium bolus.

Example 3

A potassium containing preparation of the present invention, wherein tri-potassium phosphate is used instead of potassium chloride, having the following composition is produced:
tri-potassium phosphate: 54 wt.-%
$CaCl_2 \cdot 2H_2O$: 28 wt.-%
water: 18 wt.-%

The general procedure is as follows:
Mix calcium chloride and water and heat to 72 to 80° C. until the crystal water is released and the salt is completely dissolved.

Add tri-potassium phosphate and heat until the temperature is 72 to 80° C. Maintain the mixture at this temperature under constant mixing.

The mixture now has the consistency of a thick dough, which is then formed into the shape of a bolus.

Allow cooling to room temperature (about 15 to 30° C.).

After cooling the mixture becomes a solid mass.

The solid mass which represents the potassium bolus is dipped and covered in a suitable coating material before it may be administered to a cow.

Example 4

A potassium bolus produced according to Example 1 will have a melting point of around 30° C. If a potassium bolus with a higher melting point is required the ratio between the $CaCl_2$ and water should be increased, preferably to >5:3, more preferably >5:2, which will also require a slight modification of the other ingredients.

For instance a potassium containing preparation of the present invention with a melting point of 37° C. having the following composition is produced:
Potassium chloride 49%
$CaCl_2$, 2 $H_2O$ 31%
Water 11%
Magnesium oxide 9%

The same general procedure as outlined in Example 1.

Example 5

Effects of oral supplementation of potassium in hypokalemic dairy cows by use of a bolus formulation on metabolism, abomasal motility and vaginal discharge characteristics.

The aim was to confirm the effectiveness of a dietary supplement in a bolus formulation containing potassium and magnesium in the reconvalescence of dairy cows suffering from parturient diseases that are causing moderate and severe hypokalemia in early lactation (5 days to 6 weeks postpartum) hospitalized due postpartum disorders such as ketosis, abomasal displacement and/or metritis and to evaluate the effects of potassium supplementation on metabolism, abomasal motility and vaginal discharge characteristics. The main criterion is the return of the plasma potassium level to the reference range of 3.5-5.0 mmol/1.

Setup:

Dairy cows between 5 and 42 days in lactation with hypokalemia (plasma potassium levels as determined by ion-selective electrode (ISE)<3.5 mmol/l) at admission were assigned either to a treatment group or a non-treatment control group. Animals belonging to the treatment group (group 1a) received one initial bolus containing potassium and magnesium. Animals belonging to the control group (group 1b) received no treatment unless the blood level of potassium decreased underneath 2.8 mmol/l at subsequent samplings. In those cases the animals were assigned to treatment group 2.

Drug Formulation:

Bolus containing potassium and magnesium formulated and produced in accordance with Example 1.

Route of administration: oral by balling gun

Amount of each dose: 1 Bolus at a time

Frequency of dosage: Group 1a (plasma potassium levels 2.8-3.4 mmol/l): one bolus at admission, another bolus if potassium level is below reference range 12-18 hrs later. Group 1b (plasma potassium levels 2.8-3.4 mmol/l): no bolus. Group 2 (plasma potassium <2.8 mmol/l): one bolus at admission, a second bolus after approximately 12-18 hours after arrival, a third bolus if plasma potassium level is still low 12-18 hrs later.

Result:

Data of 33 cases were available for an analysis. As shown below in Table 1 the blood potassium levels in the treatment group (1a) were on average within the reference range already 1 hr after admission whereas it took 36 hrs for the cows of the control group. The cows in group 2 (severe hypokalemia) were within the reference range after 36 hrs as well.

TABLE 1

| Group | Hour | N | Mean Potassium [mmol/l] |
|---|---|---|---|
| 1a | 0 | 16 | 3.14 |
|  | 1 | 16 | 3.63 |
|  | 2 | 16 | 3.71 |
|  | 3 | 16 | 3.88 |
|  | 12 | 16 | 3.79 |
|  | 36 | 16 | 3.96 |
|  | 84 | 16 | 3.65 |
| 1b | 0 | 12 | 3.23 |
|  | 1 | 12 | 3.12 |
|  | 2 | 12 | 3.25 |
|  | 3 | 12 | 3.23 |
|  | 12 | 12 | 3.37 |
|  | 36 | 12 | 3.81 |
|  | 84 | 12 | 3.72 |
| 2 | 0 | 5 | 2.44 |
|  | 1 | 5 | 2.66 |
|  | 2 | 5 | 2.76 |
|  | 3 | 5 | 2.88 |
|  | 12 | 5 | 3.62 |
|  | 36 | 5 | 3.96 |
|  | 84 | 4 | 4.05 |

What is claimed is:

1. A potassium containing preparation in solid bolus form and suitable for the prevention or treatment of potassium deficit and optionally other deficit of minerals in ruminants, comprising the following composition:
   potassium salt in an amount from 40 to 70 wt. %;
   $CaCl_2 \cdot xH_2O$ crystals in an amount from 15 to 40 wt. %, wherein x=0, 1, 2 or 4 or mixtures thereof; and
   mineral salt(s) other than potassium salt and calcium chloride in an amount from 0 to 15 wt. %;
   wherein the values of wt. % are based on the total weight of the potassium containing preparation, and the potassium salt is incorporated in a crystal structure formed by the $CaCl_2 \cdot xH_2O$ crystals.

2. The potassium containing preparation according to claim 1, characterized in that the potassium salt is selected from the group consisting of potassium chloride, potassium bromide, potassium iodide, potassium sulfate, potassium nitrate, potassium phosphate, di-potassium phosphate, tri-potassium phosphate, potassium citrate, and potassium citrate monohydrate.

3. The potassium containing preparation according to claim 2, characterized in that the potassium salt is water-soluble and has no crystal water in the crystallized form.

4. The potassium containing preparation according to claim 1, characterized in that the potassium salt is water-soluble and has no crystal water in the crystallized form.

5. The potassium containing preparation according to claim 1, characterized in that the mineral salt(s) is(are) selected from the group consisting of salts of copper (Cu), magnesium (Mg), iron (Fe), zinc (Zn), iodine (I), selenium (Se), manganese (Mn), fluoride (F—), chromium (Cr), molybdenum (Mo), sodium (Na), phosphorus (P), sulfur (S), chloride (Cl—), magnesium chloride, magnesium oxide, magnesium hydroxide and mixtures thereof.

6. The potassium containing preparation according to claim 1, in an oral dosage form or dietary supplement for use in a method of prevention or treatment of potassium deficit and optionally other deficit of minerals in ruminants.

7. The potassium containing preparation according to claim 1, wherein:
   the potassium salt has a concentration of >40 to 70 wt. %
   $CaCl_2 \cdot xH_2O$ has a concentration from 25 to 35 wt. %; and
   mineral salt(s) has a concentration from 0 to 12 wt. %.

8. A potassium containing preparation in solid bolus form and suitable for the prevention or treatment of potassium deficit and optionally other deficit of minerals in ruminants, comprising the following composition:
   potassium salt in an amount from 50 to 55 wt. %;
   $CaCl_2 \cdot 2H_2O$ crystals in an amount from 22 to 28 wt. %; and
   mineral salt(s) other than potassium salt and calcium chloride in an amount from 5 to 12 wt. %;
   wherein the values of wt. % are based on the total weight of the potassium containing preparation, and the potassium salt is incorporated in a crystal structure formed by the $CaCl_2 \cdot xH_2O$ crystals.

9. The potassium containing preparation according to claim 8, characterized in that the potassium salt is selected from the group consisting of potassium chloride, potassium bromide, potassium iodide, potassium sulfate, potassium nitrate, potassium phosphate, di-potassium phosphate, tri-potassium phosphate, potassium citrate, and potassium citrate monohydrate.

10. The potassium containing preparation according to claim 8, characterized in that the potassium salt is water-soluble and has no crystal water in the crystallized form.

11. The potassium containing preparation according to claim 8, characterized in that the mineral salt(s) is(are) selected from the group consisting of salts of copper (Cu), magnesium (Mg), iron (Fe), zinc (Zn), iodine (I), selenium (Se), manganese (Mn), fluoride (F—), chromium (Cr), molybdenum (Mo), sodium (Na), phosphorus (P), sulfur (S), chloride (Cl—), magnesium chloride, magnesium oxide, magnesium hydroxide and mixtures thereof.

12. The potassium containing preparation according to claim 8, characterized in that the $CaCl_2.2H_2O$ is formed by combining calcium chloride and water at a weight ratio of >5:3.

13. The potassium containing preparation according to claim 8, in an oral dosage form or dietary supplement for use in a method of prevention or treatment of potassium deficit and optionally other deficit of minerals in ruminants.

14. A potassium containing preparation in solid bolus form and suitable for the prevention or treatment of potassium deficit and optionally other deficit of minerals in ruminants, comprising the following composition:
  potassium salt in an amount from 40 to 60 wt. %;
  $CaCl_2.2H_2O$ crystals in an amount from 25 to 40 wt. %; and
  mineral salt(s) other than potassium salt and calcium chloride in an amount from 0 to 12 wt. %;
  wherein the values of wt. % are based on the total weight of the potassium containing preparation, and the potassium salt is incorporated in a crystal structure formed by the $CaCl_2.xH_2O$ crystals.

15. The potassium containing preparation according to claim 14, characterized in that the potassium salt is selected from the group consisting of potassium chloride, potassium bromide, potassium iodide, potassium sulfate, potassium nitrate, potassium phosphate, di-potassium phosphate, tri-potassium phosphate, potassium citrate, and potassium citrate monohydrate.

16. The potassium containing preparation according to claim 14, characterized in that the potassium salt is water-soluble and has no crystal water in the crystallized form.

17. The potassium containing preparation according to claim 14, characterized in that the mineral salt(s) is(are) selected from the group consisting of salts of copper (Cu), magnesium (Mg), iron (Fe), zinc (Zn), iodine (I), selenium (Se), manganese (Mn), fluoride (F—), chromium (Cr), molybdenum (Mo), sodium (Na), phosphorus (P), sulfur (S), chloride (Cl—), magnesium chloride, magnesium oxide, magnesium hydroxide and mixtures thereof.

18. The potassium containing preparation according to claim 14, characterized in that the $CaCl_2.2H_2O$ is formed by combining calcium chloride and water at a weight ratio of >5:3.

19. The potassium containing preparation according to claim 14, wherein the bolus is in an oral dosage form or dietary supplement for use in a method of prevention or treatment of potassium deficit and optionally other deficit of minerals in ruminants.

20. A potassium containing preparation in solid bolus form and suitable for the prevention or treatment of potassium deficit and optionally other deficit of minerals in ruminants, comprising the following composition:
  potassium salt present in an amount of 50 to 60 wt. %;
  $CaCl_2.xH_2O$ crystals present in an amount of 15 to 40 wt. %, wherein x=0, 1, 2 or 4 or mixtures thereof; and
  mineral salt(s) other than potassium salt and calcium chloride, the mineral salt(s) in an amount of 0 to 15 wt. %;
  wherein the values of wt. % are based on the total weight of the potassium containing preparation, and the potassium salt is incorporated in a crystal structure formed by the $CaCl_2.xH_2O$ crystals.

21. The potassium containing preparation according to claim 20, characterized in that the potassium salt is selected from the group consisting of potassium chloride, potassium bromide, potassium iodide, potassium sulfate, potassium nitrate, potassium phosphate, di-potassium phosphate, tri-potassium phosphate, potassium citrate, and potassium citrate monohydrate.

22. The potassium containing preparation according to claim 20, characterized in that the potassium salt is water-soluble and has no crystal water in the crystallized form.

23. The potassium containing preparation according claim 20, characterized in that the mineral salt(s) is(are) selected from the group consisting of salts of copper (Cu), magnesium (Mg), iron (Fe), zinc (Zn), iodine (I), selenium (Se), manganese (Mn), fluoride (F—), chromium (Cr), molybdenum (Mo), sodium (Na), phosphorus (P), sulfur (S), chloride (Cl—), magnesium chloride, magnesium oxide, magnesium hydroxide and mixtures thereof.

24. The potassium containing preparation according to claim 20, wherein the bolus is in an oral dosage form or dietary supplement for use in a method of prevention or treatment of potassium deficit and optionally other deficit of minerals in ruminants.

25. The potassium containing preparation according to claim 20, wherein:
  the $CaCl_2.xH_2O$ has a concentration from 25 to 35 wt. %; and
  mineral salt(s) has a concentration from 0 to 12 wt. %.

26. A process for the production of the potassium containing preparation according to claim 1, comprising the following steps:
  (a) mixing $CaCl_2.xH_2O$, wherein x=0, 1, 2 or 4 or mixtures thereof, and water and heating the mixture to a temperature in the range of from 65 to 100° C. until the crystal water is released and the salt is completely dissolved;
  (b) adding a potassium salt and optionally one or more mineral salts wherein the mineral salts are other than potassium salt and calcium chloride, and heating until the temperature is again in the range of from 65 to 100° C.;
  (c) maintaining the mixture at the temperature adjusted in step (b) under mixing to keep the potassium salt and optionally the one or more mineral salts in a homogeneous suspension; and
  (d) forming the suspension into a suitable form and cooling to a temperature in the range of from 15° C. to 30° C. to obtain a solid mass.

27. The process according to claim 26, characterized in that the potassium salt is added in an amount of 40 to 70 wt. % based on the total weight of the potassium containing preparation.

28. The process according to claim 26, characterized in that the potassium salt used is selected from potassium chloride, potassium bromide, potassium iodide, potassium sulfate, potassium nitrate, potassium phosphate, di-potassium phosphate, tri-potassium phosphate, potassium citrate, and potassium citrate monohydrate.

29. The process according to claim 26, characterized in that the potassium salt is water-soluble and has no crystal water in the crystallized form.

30. The process according to claim 26, characterized in that the mineral salt(s) is(are) selected from the group consisting of salts of copper (Cu), magnesium (Mg), iron (Fe), zinc (Zn), iodine (I), selenium (Se), manganese (Mn), fluoride (F⁻), chromium (Cr), molybdenum (Mo), sodium (Na), phosphorus (P), sulfur (S) and/or chloride (Cl⁻), and mixtures thereof.

31. The process according to claim 26, characterized in that the temperature in steps (a), (b) and (c) is below 100° C.

32. The process according to claim 26, characterized in that in an additional step (e) the solid mass obtained in step (d) is subjected to an additional coating step.

* * * * *